US012740822B2

(12) United States Patent
Allen, IV et al.

(10) Patent No.: US 12,740,822 B2
(45) Date of Patent: Sep. 22, 2026

(54) THERMAL CUTTING ASSEMBLY WITH CONDUCTIVE BRIDGE

(71) Applicant: Covidien LP, Mansfield, MA (US)

(72) Inventors: James D. Allen, IV, Boulder, CO (US); Kenneth E. Netzel, Boulder, CO (US); William E. Robinson, Boulder, CO (US); Craig C. Sundberg, Erie, PA (US)

(73) Assignee: Covidien LP, Mansfield, MA (US)

(*) Notice: Subject to any disclaimer, the term of this patent is extended or adjusted under 35 U.S.C. 154(b) by 159 days.

(21) Appl. No.: 18/852,774

(22) PCT Filed: Mar. 31, 2023

(86) PCT No.: PCT/IB2023/053245
§ 371 (c)(1),
(2) Date: Sep. 30, 2024

(87) PCT Pub. No.: WO2023/187735
PCT Pub. Date: Oct. 5, 2023

(65) Prior Publication Data

US 2025/0221756 A1 Jul. 10, 2025

Related U.S. Application Data

(60) Provisional application No. 63/325,698, filed on Mar. 31, 2022.

(51) Int. Cl.
*A61B 18/14* (2006.01)
*A61B 18/08* (2006.01)
(Continued)

(52) U.S. Cl.
CPC .. *A61B 18/085* (2013.01); *A61B 2017/00526* (2013.01); *A61B 2018/00077* (2013.01);
(Continued)

(58) Field of Classification Search
CPC ................ A61B 18/082; A61B 18/085; A61B 2017/00526; A61B 2018/00077;
(Continued)

(56) References Cited

U.S. PATENT DOCUMENTS 6,602,252 B2 * 8/2003 Mollenauer .......... A61B 18/085 606/49
2005/0288747 A1 12/2005 Aoki et al.
(Continued)

FOREIGN PATENT DOCUMENTS

WO 2022/164622 A1 8/2022

OTHER PUBLICATIONS

International Search Report for International Application No. PCT/IB2023/053245 mailed Jul. 20, 2023 (3 pages).
(Continued)

*Primary Examiner* — Michael F Peffley

(57) ABSTRACT

A thermal cutting assembly for a jaw member includes a substrate having a cutting edge disposed along an upper surface thereof. An insulator is disposed along the sides of the substrate and extends therealong. A first and second resistive elements connect to an energy source and are disposed in thermal communication on either side of the substrate atop the insulator. The distal end of each resistive element is exposed from the insulator and electrically connects to the substrate. The substrate forms a conductive bridge between the distal ends of the first and second resistive elements.

17 Claims, 12 Drawing Sheets

(51) Int. Cl.
*A61B 17/00* (2006.01)
*A61B 18/00* (2006.01)
*A61B 34/35* (2016.01)

(52) U.S. Cl.
CPC ............... *A61B 2018/00083* (2013.01); *A61B 2018/00601* (2013.01); *A61B 2018/0063* (2013.01); *A61B 34/35* (2016.02)

(58) Field of Classification Search
CPC ........... A61B 2018/00083; A61B 2018/00095; A61B 2018/00601; A61B 2018/00607; A61B 2018/0063; A61B 2018/00994; A61B 34/35; A61B 34/37
See application file for complete search history.

(56) References Cited

U.S. PATENT DOCUMENTS

2019/0192209 A1 6/2019 Eggers et al.
2021/0186587 A1* 6/2021 Robinson ............... A61B 18/08
2023/0240740 A1* 8/2023 Robinson ............. A61B 18/085
606/29

OTHER PUBLICATIONS

International Written Opinion for International Application No. PCT/IB2023/053245 mailed Jul. 20, 2023 (8 pages).

* cited by examiner

THERMAL CUTTING ASSEMBLY WITH CONDUCTIVE BRIDGE

CROSS-REFERENCE TO THE RELATED APPLICATIONS

This application is a National Stage of PCT/IB2023/053245 filed on Mar. 31, 2023, which claims the benefit of and priority to U.S. Provisional Patent Application Ser. No. 63/325,698, filed on Mar. 31, 2022, the entire disclosure of which is are incorporated by reference herein in their entireties. To the extent appropriate, a claim of priority is made to each of the above disclosed applications.

FIELD

The present disclosure relates to surgical instruments and, more particularly, to electrosurgical instruments for sealing and cutting tissue utilizing a thermal cutting element.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element or thermal cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a thermal cutting assembly for a jaw member of a surgical instrument which includes an elongated substrate having proximal and distal ends and a cutting edge disposed along an upper surface thereof. A dielectric insulator is disposed along first and second sides of the substrate and extends partially or fully therealong from the proximal end to the distal end thereof. A first resistive element is adapted to connect to an energy source and is disposed in thermal communication with the substrate. The first resistive element is configured to extend along the dielectric insulator on the first side of the substrate to a distal end portion, the first resistive element including a distal end exposed from the dielectric insulator and in electrical communication with the substrate. A second resistive element is adapted to connect to the energy source and is disposed in thermal communication with the substrate, the second resistive element is configured to extend along the dielectric insulator on a second side of the substrate to the distal end portion, the second resistive element including a distal end exposed from the dielectric insulator and in electrical communication with the substrate. The substrate forms a conductive bridge between the distal ends of the first and second resistive elements.

In aspects in accordance with the present disclosure, an encapsulant is disposed atop the dielectric insulator, the first and second resistive elements and the conductive bridge.

In aspects in accordance with the present disclosure, one or both of the first or second resistive elements includes one or more of aluminum, copper, silver, chromium, titanium, stainless steel, nickel, chrome, tin, platinum, palladium, gold, nichrome, and a ferritic iron-chromium-aluminum alloy.

In aspects in accordance with the present disclosure, a hook is disposed at the distal end of the substrate, the hook defining a notch configured to operably engage a portion of the jaw member for securing the substrate therein. In other aspects in accordance with the present disclosure, the conductive bridge is disposed on the hook. In yet other aspects in accordance with the present disclosure, a distal end of the hook is exposed relative to the dielectric insulator and in electrical communication with the distal ends of both the first and second resistive elements forming the conductive bridge. In still other aspects in accordance with the present disclosure, the hook defines a notch configured to operably engage a first portion of the jaw member and wherein the conductive bridge defines a portion of the notch.

Provided in accordance with aspects of the present disclosure is a thermal cutting assembly for a jaw member of a surgical instrument which includes an elongated substrate including proximal and distal ends, a cutting edge disposed along an upper surface thereof, and a through-hole defined through the distal end thereof. A dielectric insulator disposed along first and second sides of the substrate and extending at least partially therealong from the proximal end to the distal end thereof. A first resistive element connects to an energy source and is disposed in thermal communication with the substrate, the first resistive element is configured to extend along the dielectric insulator on a first side of the substrate to the through-hole. The first resistive element includes a distal end disposed in electrical communication with a conductive bridge disposed within the through-hole of the substrate. A second resistive element connects to the energy source and is disposed in thermal communication with the substrate, the second resistive element is configured to extend along the dielectric insulator on a second side of the substrate to the through-hole. The second resistive element includes a distal end disposed in electrical communication with the first resistive element via the conductive bridge of the substrate.

In aspects in accordance with the present disclosure, an encapsulant is disposed atop the dielectric insulator, the first and second resistive elements and the conductive bridge.

In aspects in accordance with the present disclosure, one or both of the first or second resistive elements includes one or more of aluminum, copper, silver, chromium, titanium, stainless steel, nickel, chrome, tin, platinum, palladium, gold, nichrome, and a ferritic iron-chromium-aluminum alloy.

In aspects in accordance with the present disclosure, a hook is disposed at the distal end of the substrate, the hook defining a notch configured to operably engage a portion of the jaw member for securing the substrate therein. In other aspects in accordance with the present disclosure, the through-hole is distal to the hook.

Provided in accordance with aspects of the present disclosure is a method of manufacturing a thermal cutting assembly for a jaw member of a surgical instrument which includes: disposing a dielectric insulator along first and second sides of a substrate from a proximal end to a distal end thereof, the substrate including a cutting edge disposed along an upper surface thereof and a through-hole defined through the distal end thereof; depositing a first resistive element on a first side of the substrate atop the dielectric insulator, the first resistive element connects to an energy source and is disposed in thermal communication with the substrate, the first resistive element including a distal end disposed in electrical communication with a conductive bridge disposed within the through-hole of the substrate; depositing a second resistive element on a second side of the substrate atop the dielectric insulator, the second resistive element connects to the energy source and is disposed in thermal communication with the substrate, the second resistive element including a distal end disposed in electrical communication with the first resistive element via the conductive bridge of the substrate.

In aspects in accordance with the present disclosure, the method further includes depositing an encapsulant atop the dielectric material, the first and second resistive elements and the conductive bridge.

In aspects in accordance with the present disclosure, one or more of the first or second resistive element includes one or more of aluminum, copper, silver, chromium, titanium, stainless steel, nickel, chrome, tin, platinum, palladium, gold, nichrome, and a ferritic iron-chromium-aluminum alloy.

In aspects in accordance with the present disclosure, the method further includes operably engaging a notch defined within a hook portion of the jaw member to secure the substrate therein. In other aspects in accordance with the present disclosure, the through-hole is distal to the hook portion.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
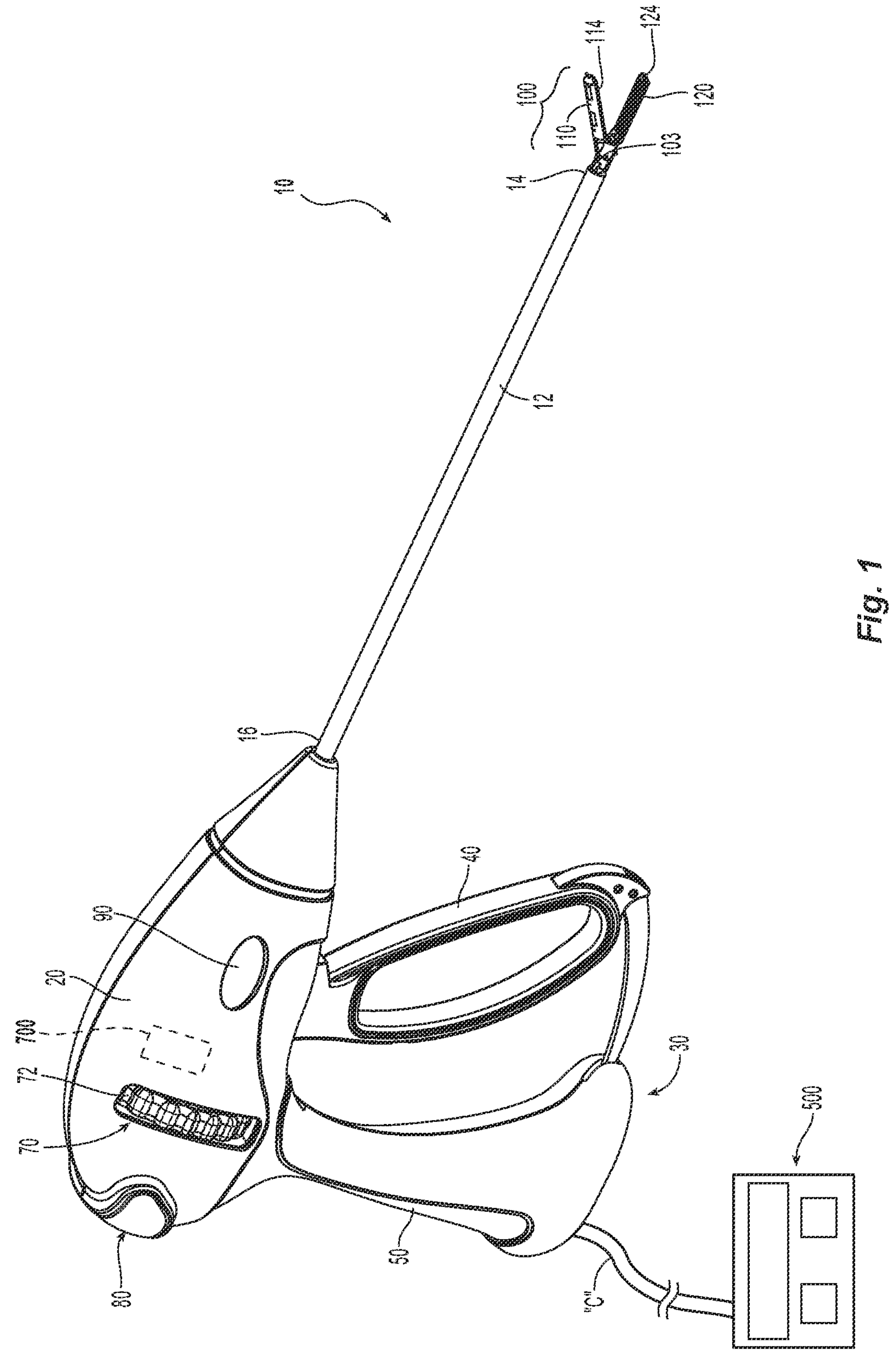
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a rotating assembly 70, a first activation switch 80, a second activation switch 90, and an end effector assembly 100. As shown, end effector assembly 100 includes jaw members 110 and 120 configured for unilateral movement relative to one another. Bilateral movement of the jaw members 110, 120 is also envisioned. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 (see FIG. 4) to provide energy thereto.

First activation switch 80 is coupled to tissue-treating surfaces 114, 124 (FIG. 4) and the electrosurgical generator "G" for enabling the selective activation of the supply of energy to jaw members 110, 120 for treating, e.g., cauterizing, coagulating/desiccating, and/or sealing, tissue. Second activation switch (e.g., thumb switch 90) is coupled to thermal cutter assembly 130 of jaw member 120 (FIG. 4) and the electrosurgical generator "G" for enabling the selective activation of the supply of energy to thermal cutter assembly 130 for thermally cutting tissue. Second activation switch 90 may be actuated via any finger, in-line with handle, footswitch, etc.

Alternatively, a single activation switch may be utilized wherein the generator "G" sequentially seals and then cuts with a single actuation of the switch, e.g., switch 80. A "seal" may be indicated by an audible tone from the generator "G" and after a short or programmable delay the forceps 10 (or the generator algorithm) transitions into a cut cycle or cut "mode". Again a "cut" may be represented by a different tone from the generator "G" or from the forceps 10.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 2:
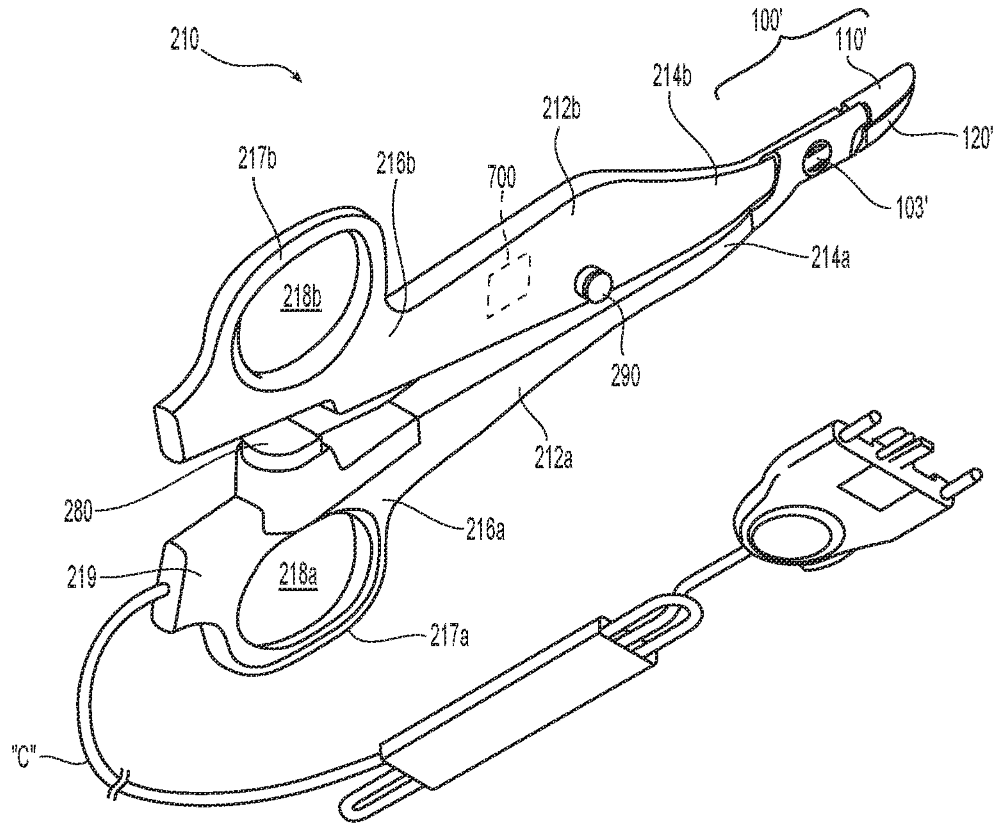
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
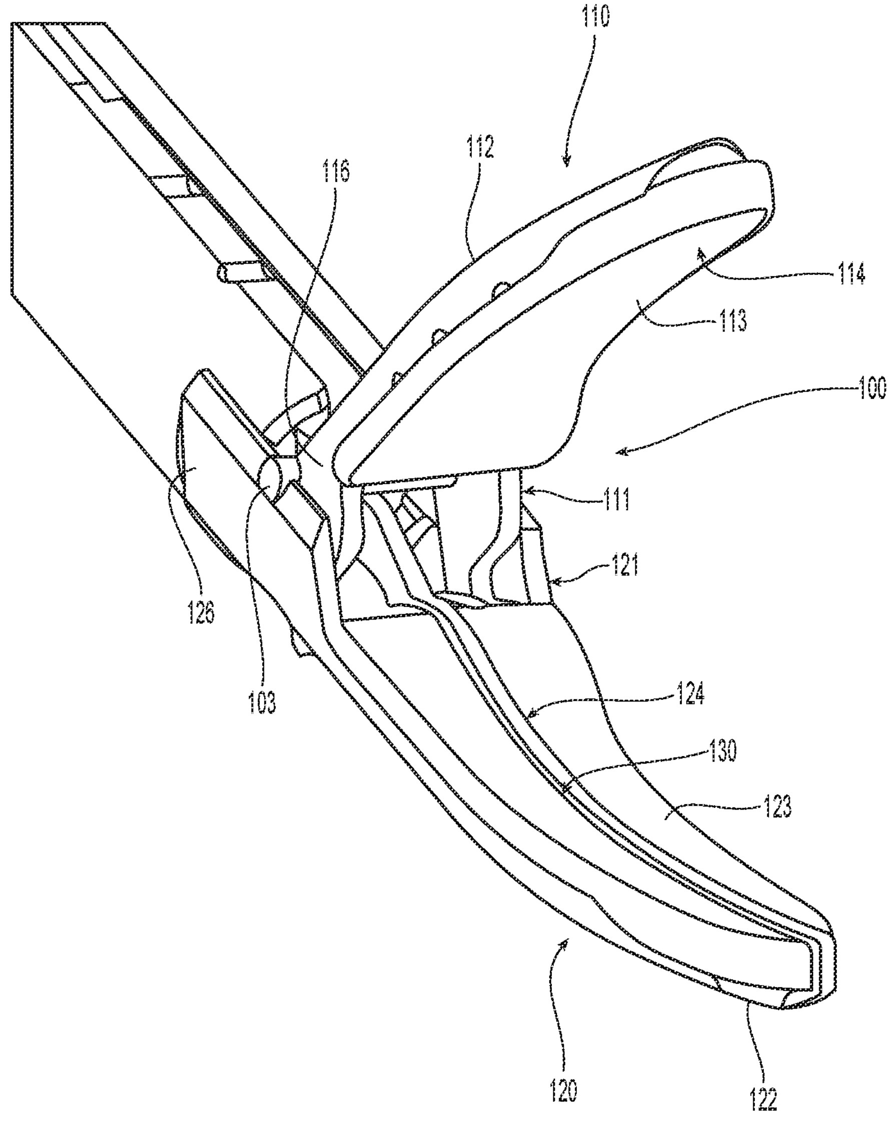
FIG. 4 is a perspective view of a distal end portion of the forceps of FIG. 1, wherein first and second jaw members of an end effector assembly of the forceps are disposed in a spaced-apart position exposing a thermal cutter assembly.

Forceps 210 includes two elongated shaft members 212*a*, 212*b*, each having a proximal end portion 216*a*, 216*b*, and a distal end portion 214*a*, 214*b*, respectively. Forceps 210 is configured for use with an end effector assembly 100' similar to end effector assembly 100 (FIG. 4). More specifically, end effector assembly 100' includes first and second jaw members 110', 120' attached to respective distal end portions 214*a*, 214*b* of shaft members 212*a*, 212*b*. Jaw members 110', 120' are pivotably connected about a pivot 103'. Each shaft member 212*a*, 212*b* includes a handle 217*a*, 217*b* disposed at the proximal end portion 216*a*, 216*b* thereof. Each handle 217*a*, 217*b* defines a finger hole 218*a*, 218*b* therethrough for receiving a finger of the user. As can be appreciated, finger holes 218*a*, 218*b* facilitate movement of the shaft members 212*a*, 212*b* relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212*a*, 212*b* of forceps 210, e.g., shaft member 212*b*, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 (similar to activation switch 80 discussed above) is provided for supplying energy to jaw members 110', 120' to treat tissue upon sufficient approximation of shaft members 212*a*, 212*b*, e.g., upon activation of first activation switch 280 via shaft member 212*a*. A second activation switch 290 (similar to second activation switch 90 discussed above) disposed on either or both of shaft members 212*a*, 212*b* is coupled to the thermal cutter element (not shown, similar to thermal cutter assembly 130 of jaw member 120 (FIG. 4)) of one of the jaw members 110', 120' of end effector assembly 100' and to the electrosurgical generator "G" for enabling the selective activation of the supply of energy to the thermal cutter assembly 130 for thermally cutting tissue.

Alternatively, a single activation switch may be utilized wherein the generator "G" sequentially seals and then cuts with a single actuation of the switch, e.g., switch 280. A "seal" may be indicated by an audible tone from the generator "G" and after a short or programmable delay the forceps 210 (or the generator algorithm) transitions into a cut cycle or cut "mode". Again a "cut" may be represented by a different tone from the generator "G" or from the forceps 210.

Jaw members 110', 120' define a curved configuration wherein each jaw member is similarly curved laterally relative to a longitudinal axis of end effector assembly 100'. However, other suitable curved configurations including curvature towards one of the jaw members 110, 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
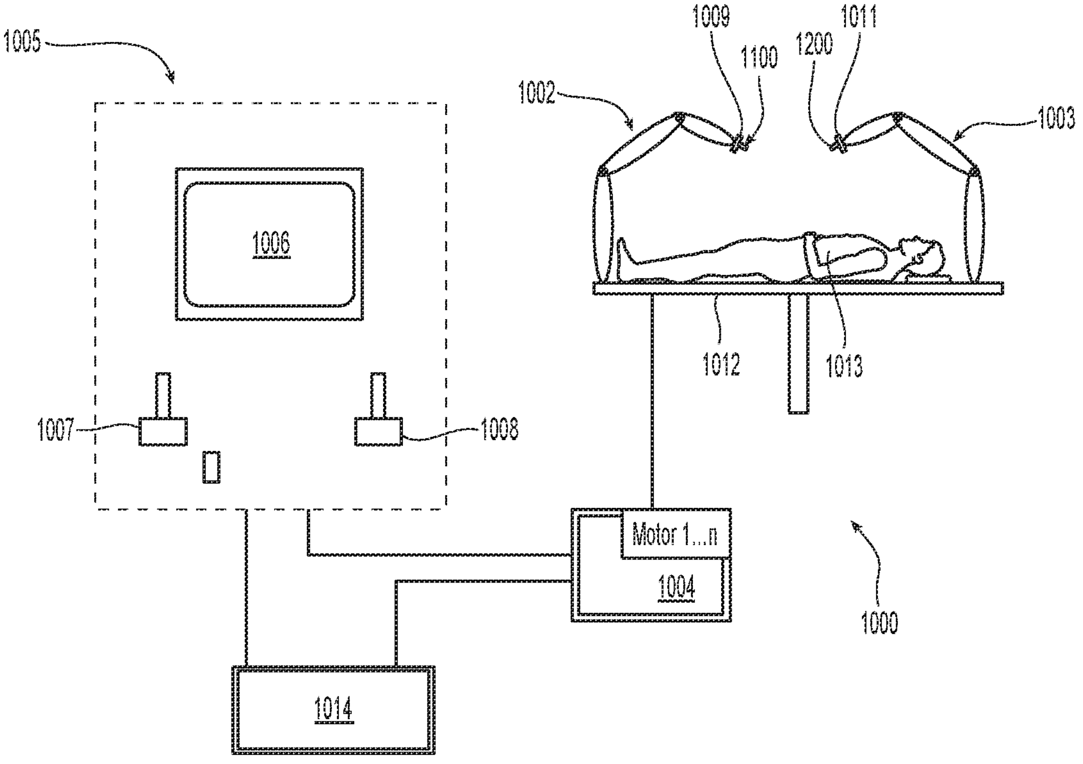
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIG. 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
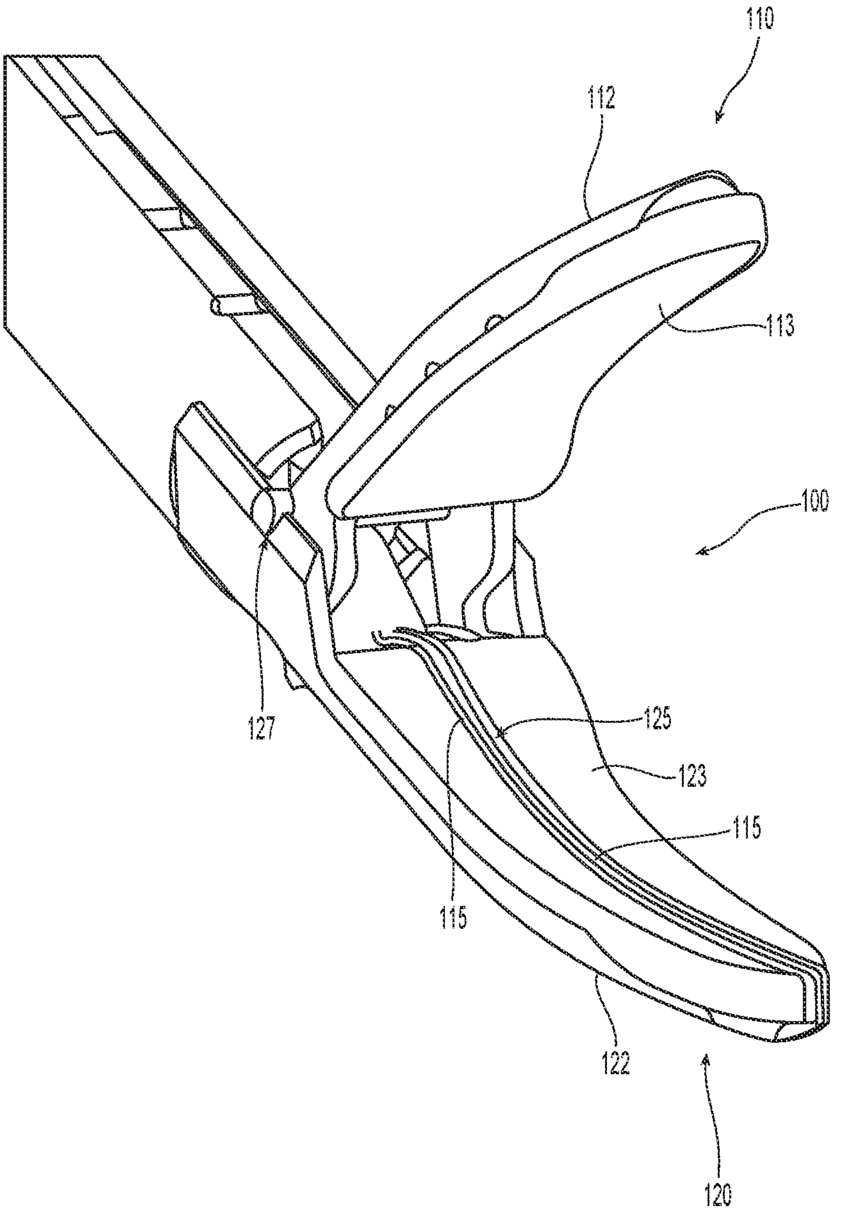
FIG. 5 is a perspective view of a distal end portion of the forceps of FIG. 1, wherein first and second jaw members of the end effector assembly of the forceps are disposed in a spaced-apart position and the thermal cutter assembly is separated therefrom exposing a slot defined in one of the jaw members.

Turning to FIGS. 4-5, end effector assembly 100, as noted above, includes first and second jaw members 110, 120. Each jaw member 110, 120 may include a structural frame 111, 121, a jaw housing 112, 122, and a tissue-treating plate 113, 123 defining the respective tissue-treating surface 114, 124 thereof. Alternatively, only one of the jaw members, e.g., jaw member 120, may include structural frame 121, jaw housing 122, and tissue-treating plate 123 defining the tissue-treating surface 124. In such embodiments, the other jaw member, e.g., jaw member 110, may be formed as a single unitary body, e.g., a piece of conductive material acting as the structural frame 111 and jaw housing 112 and defining the tissue-treating surface 114.

An outer surface of the jaw housing 112, in such embodiments, may be at least partially coated with an electrically insulative material or may remain exposed. In embodiments, tissue-treating plates 113, 123 may be deposited onto jaw housings 112, 122 or jaw inserts (not shown) disposed within jaw housings 112, 122, e.g., via sputtering. Alternatively, tissue-treating plates 113, 123 may be pre-formed and engaged with jaw housings 112, 122 and/or jaw inserts (not shown) disposed within jaw housings 112, 122 via, for example, overmolding, adhesion, mechanical engagement, etc. Other methods of depositing the tissue-treating plates 113, 123 onto the jaw inserts are described in detail below.

Referring in particular to FIGS. 4 and 5, jaw member 110, as noted above, may be configured similarly as jaw member 120, may be formed as a single unitary body, or may be formed in any other suitable manner so as to define a structural frame 111 and a tissue-treating surface 114 opposing tissue-treating surface 124 of jaw member 120. Structural frame 111 includes a proximal flange portion 116 about which jaw member 110 is pivotably coupled to jaw member 120. In shaft-based or robotic embodiments, proximal flange portion 116 receives pivot 103 and which mounts atop flange 126 of jaw member 120 (FIG. 4) such that actuation of movable handle 40 (FIG. 1) or a robotic drive, pivots jaw member 110 about pivot 103 and relative to jaw member 120 between the spaced-apart position and the approximated position. However, other suitable drive arrangements are also contemplated, e.g., using cam pins and cam slots, a screw-drive mechanism, etc.

For the purposes of further describing one or both of the jaw members 110, 120 (and 210, 220), each jaw member 110, 120 may include a longitudinally-extending insulative member 115 defined within a slot 125 extending along at least a portion of the length of tissue-treating surfaces 114, 124 (FIG. 5). Insulative member 115 may be transversely centered on either or both tissue-treating surfaces 114, 124 or may be offset relative thereto. As explained in more detail below with respect to jaw member 120, insulative member 115 may house and electrically and/or thermally isolate the thermal cutter assembly 130 separately activatable to cut tissue upon activation thereof. Further, insulative member 115 may be disposed, e.g., deposited, coated, etc., on tissue-treating surface 114, 124, may be positioned within the channel or recess defined within tissue-treating surface 114, 124, or may define any other suitable configuration.

Additionally, insulative member 115 may be substantially (within manufacturing, material, and/or use tolerances) coplanar with each respective tissue-treating surface 114, 124 may protrude from each respective tissue-treating surface 114, 124, may be recessed relative to each respective tissue-treating surface 114, 124 or may include different portions that are coplanar, protruding, and/or recessed relative to tissue-treating surfaces 114, 124. Moreover, insulative member 115 and thermal cutter assembly 130 may be curvilinear to follow the configuration of the jaw members 110, 120. Insulative member 115 may be formed from, for example, ceramic, parylene, glass, nylon, PTFE, or other suitable material(s) (including combinations of insulative and non-insulative materials).

Figure 6A:
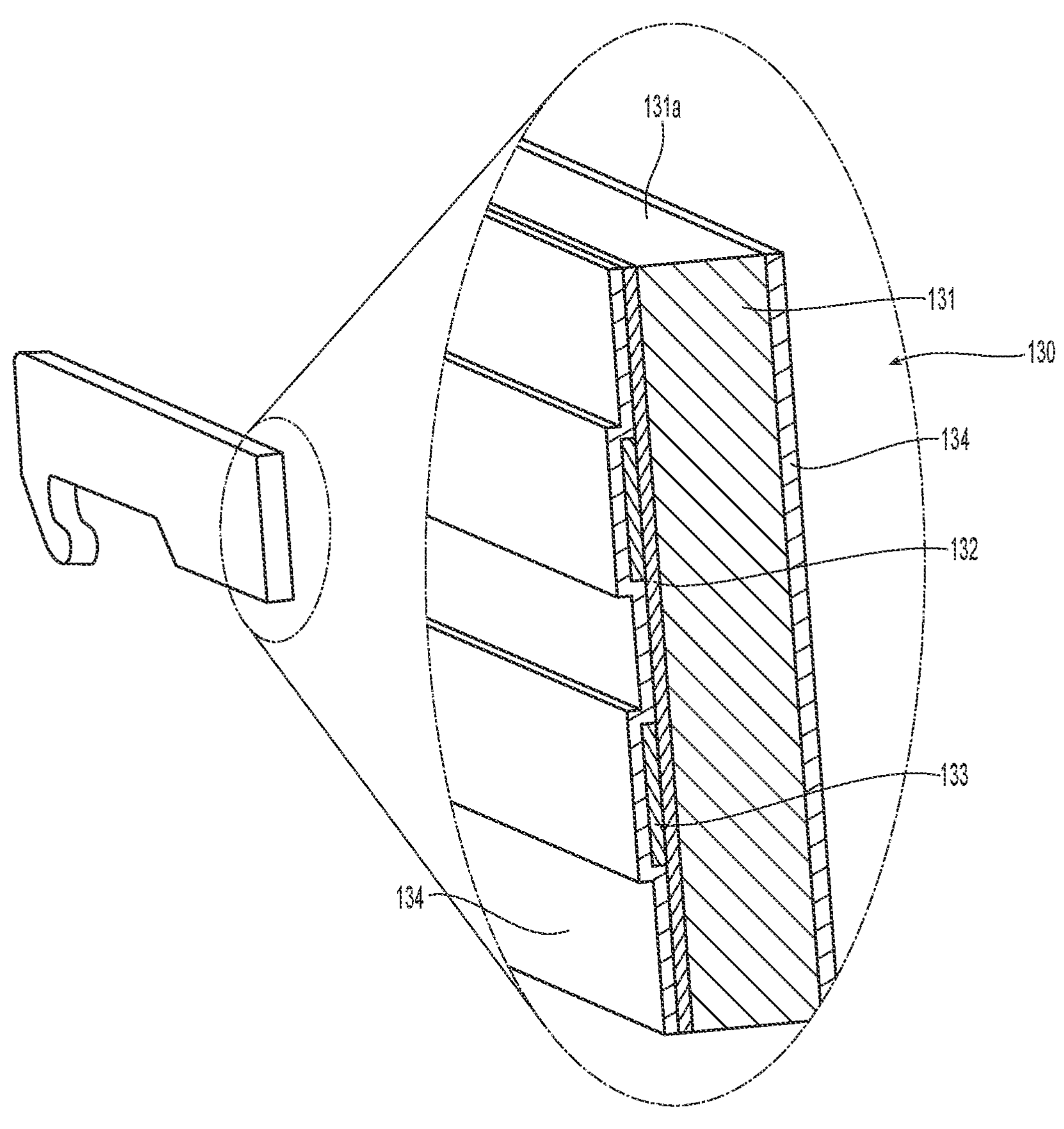
FIG. 6A is a schematic view of the thermal cutter assembly in accordance with the present disclosure.

With reference to FIGS. 4 and 5, as noted above, jaw member 120 includes a structural frame 121, a jaw housing 122, and a tissue-treating plate 123 defining the tissue-treating surface 124 thereof. With reference also to FIG. 6A, details relating to the thermal cutter assembly 130 are generally defined to include the following elements (described internally to externally): substrate 131 or other internalized bendable metal structure that is both thermally and electrically conductive, e.g., stainless steel, aluminum, etc.; insulator 132 having generally electrically insulative properties and at least partially conductive, e.g., sintered glass, alumina, plasma electrolytic oxidation (PEO anodize), Silica, etc.; resistive element 133 or any metal that is resistive but certain metals may have better thermal coefficients than others; and encapsulant 134 or an electrically insulative materials that is at least partially thermally conductive (may be the same or similar to the insulator). As explained below, the resistive element 133 may be deposited atop insulator 132 via sputtering or the like.

Figure 6B:
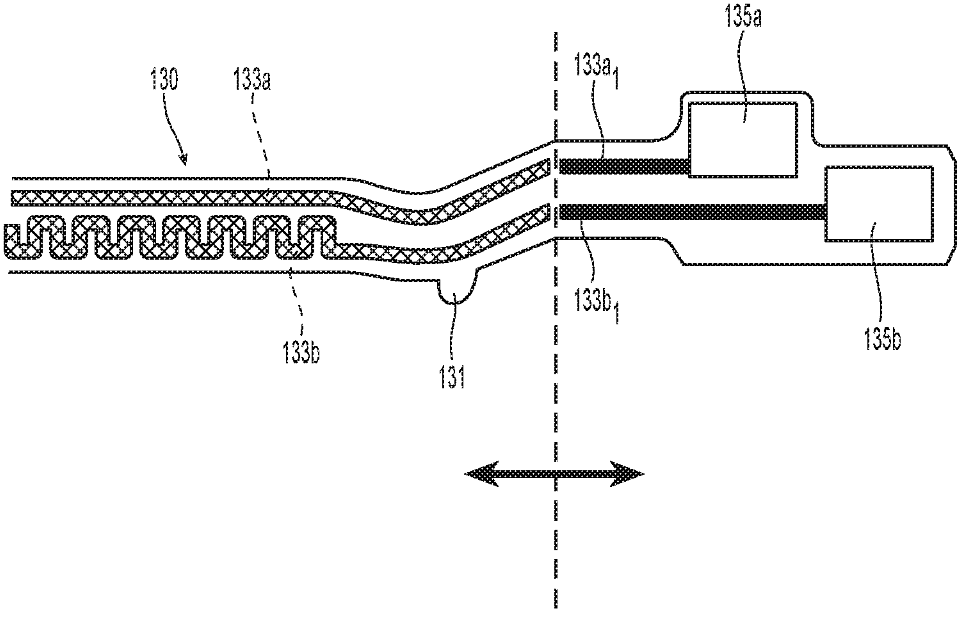
FIG. 6B is a schematic side view of the thermal cutter assembly in accordance with the present disclosure.

FIG. 6B shows a side view of thermal cutter assembly 130 and the electrical connections associated therewith. Generally, electrically conductive pads **135*a*, 135*b* connect to opposite ends 133*a*, 133*b* of resistive element 133 via traces 133*a*1, 133*b*1 which are electrically conductive traces (low resistance/low heat). As explained in detail below, resistive element 133** is configured to rapidly generate heat due to high resistive properties when electrical current is passed therethrough.

Structural frame 121 defines a proximal flange portion 126 and a distal body portion (not shown) extending distally from proximal flange portion 126. Proximal flange portion 126 is bifurcated to define a pair of spaced-apart proximal flange portion segments that receive proximal flange 111 of jaw member 110 therebetween and define aligned apertures 127 configured for receipt of pivot 103 therethrough/thereon to pivotably couple jaw members 110, 120 with one another (FIG. 5).

Jaw housing 122 of jaw member 120 is disposed about the distal body portion of structural frame 121, e.g., via overmolding, adhesion, mechanical engagement, etc., and supports tissue-treating plate 123 thereon, e.g., via overmolding, adhesion, mechanical engagement, depositing (such as, for example, via sputtering or thermal spraying), etc. Tissue-treating plate 123, as noted above, defines tissue-treating surface 124. Longitudinally-extending slot or channel 125 is defined through tissue-treating plate 123 and is positioned relative to jaw member 110 or an insulative member 115 disposed in vertical registration therewith when the jaw members 110 and 120 are in the approximated position (FIG. 5). The slot or channel 125 may be defined within an integrally-formed tissue-treating plate 123 or may be defined between two tissue-treating plates that, together, operate as a single treatment surface (not shown). Slot 125 may extend through at least a portion of jaw housing 122, a jaw insert (if so provided), and/or other components of jaw member 120 to enable receipt of thermal cutter assembly 130 at least partially within slot 125.

Thermal cutter assembly 130, more specifically, is disposed within longitudinally-extending slot 125 such that thermal cutter assembly 130 opposes jaw member 110 in the approximated position. Thermal cutter assembly 130 may be configured to contact jaw member 110 (or another insulative member 115 as mentioned above and as shown in FIG. 4) in the approximated position to regulate or contribute to regulation of a gap distance between tissue-treating surfaces 114, 124 in the approximated position. Alternatively or additionally, one or more stop members (not shown) associated with jaw member 110 and/or jaw member 120 may be provided to regulate the gap distance between tissue-treating surfaces 114, 124 in the approximated position.

Thermal cutter assembly 130 may be surrounded by the insulative member 115 disposed within slot 125 to electrically and/or thermally isolate thermal cutter assembly 130 from tissue-treating plate 123 (See FIG. 4 versus FIG. 5). As mentioned above, thermal cutter assembly 130 includes an encapsulant 134 that may act in conjunction with or in lieu of insulative member 115. Encapsulant 134 (and insulator 132 as shown in FIG. 6A) is configured cover the sides of the substrate 131 leaving the tissue facing edge 131*a* of the substrate 131 exposed. Thermal cutter assembly 130 and insulative member 115 may similarly or differently be substantially (within manufacturing, material, and/or use tolerances) coplanar with tissue-treating surface 124, may protrude from tissue-treating surface 124, may be recessed relative to tissue-treating surface 124, or may include different portions that are coplanar, protruding, and/or recessed relative to tissue-treating surface 124.

Turning back to the thermal cutter assembly 130 and the various methods of manufacturing the same, it is contemplated that the resistive element 133 of the thermal cutter assembly 130 may be manufactured in thin layers that are deposited atop (or otherwise) insulator 132 which is disposed atop substrate 131. For the purposes herein, the resistive element 133 will be described as being deposited onto insulator 132, knowing that insulator, in turn, may be disposed on one or both sides of substrate 131. For example, it is contemplated that resistive element 133 may be deposited onto the insulator 132 via one or more of the following manufacturing techniques: sputtering, thermal evaporation, thermal spraying, cathodic arcing, pulsed laser deposition, electron beam deposition. Other techniques may include: electroless strike or plating and electro-plating, shadow masking.

Utilizing one or more of these techniques provides a thin layer of thermally conductive resistive material which has the benefit of dissipating heat quickly compared to a traditional thermal cutter assembly 130. Other advantages of thin-layered resistive elements 133 on the thermal cutter assembly 130 include: the ability to heat up quickly, the ability to require less energy to heat up and maintain heat during the cutting process, and the ability to cut tissue in a reduced timeframe compared to traditional electrical cutters.

Any one of the following materials (or combinations thereof) may be utilized as the resistive element 133: aluminum, copper, chromium, titanium, stainless steel, nickel, chrome, tin, platinum, palladium, gold, nichrome, and Kanthal®. It is contemplated that during manufacturing, combinations of materials may be utilized for a particular purpose or to achieve a particular result. For example, one material may be utilized as a base conductor with a second material used as an outer or inner conductor to act as the heating element. Additional techniques or materials may be added to act as thermal cutter assemblies 130 or resistive elements 133 such as those described with reference to U.S. patent application Ser. No. 16/785,347 filed Feb. 7, 2020, U.S. Provisional Patent Application Ser. No. 62/952,232 filed Dec. 21, 2019, U.S. patent application Ser. No. 16/838,551 filed Apr. 2, 2020, and U.S. patent application Ser. No. 16/518,016 filed Jul. 22, 2019, the entire contents of each of which being incorporated by reference herein.

In other embodiments, materials may be mixed during the application process. In some embodiments, the material used (e.g., Aluminum, copper etc.,) may be thin and still promote a good cutting effect while other materials may have to be thicker to produce the same or similar cutting effect due to the particular material's level of electrical resistance. In this latter instance, a highly conductive base material may be utilized with the thinner, less conductive material more resistive material to produce a desired effect.

In embodiments, a biocompatible material (not shown) may be utilized to cover a non-biocompatible material. In other embodiments, the materials may be deposited (or otherwise disposed on insulator 132 in non-uniform layers while still allowing for transitions, e.g., side-to-side transitions. The materials could be deposited (or otherwise disposed on insulator 132) in an alternating fashion and more than one electrical circuit may be employed.

Examples of resistive elements 133 that may be used for thermal cutter assemblies 130 may include single layer resistive elements 133 in the range of about 0.1 micron to about 500 microns. A so-called "thick" film resistive element 133 would be about 30 microns and a "thin" film resistive element 133 would be about 1 micron. Non-conductive, electrically transparent, thermally transparent, or electrically and/or thermally porous materials may also be layered in a similar fashion atop, below or between the resistive elements 133. One or more of these materials may be layered atop the resistive elements 133 to complete the thermal cutter assembly 130 as mentioned above within a specified range.

Generally, tissue-treating plates 113, 123 are formed from an electrically conductive material, e.g., for conducting electrical energy therebetween for treating tissue, although tissue-treating plates 113, 123 may alternatively be configured to conduct any suitable energy, e.g., thermal, microwave, light, ultrasonic, etc., through tissue grasped therebetween for energy-based tissue treatment. As mentioned above, tissue-treating plates 113, 123 are coupled to activation switch 80 and electrosurgical generator "G" (FIG. 1) such that energy may be selectively supplied to tissue-treating plates 113, 123 and conducted therebetween and through tissue disposed between jaw members 110, 120 to treat tissue, e.g., seal tissue on either side and extending across thermal cutter assembly 130.

Thermal cutter assembly 130, on the other hand, is configured to connect to electrosurgical generator "G" (FIG. 1) and second activation switch 90 to enable selective activation of the supply of energy to thermal cutter assembly 130 for heating resistive element 133 which, in turn, heats edge 131*a* of substrate 131 to thermally cut tissue disposed between jaw members 110, 120, e.g., to cut the sealed tissue into first and second sealed tissue portions. Other configurations including multi-mode switches, other separate switches, etc. may alternatively be provided.

Figures 7A, 7B:
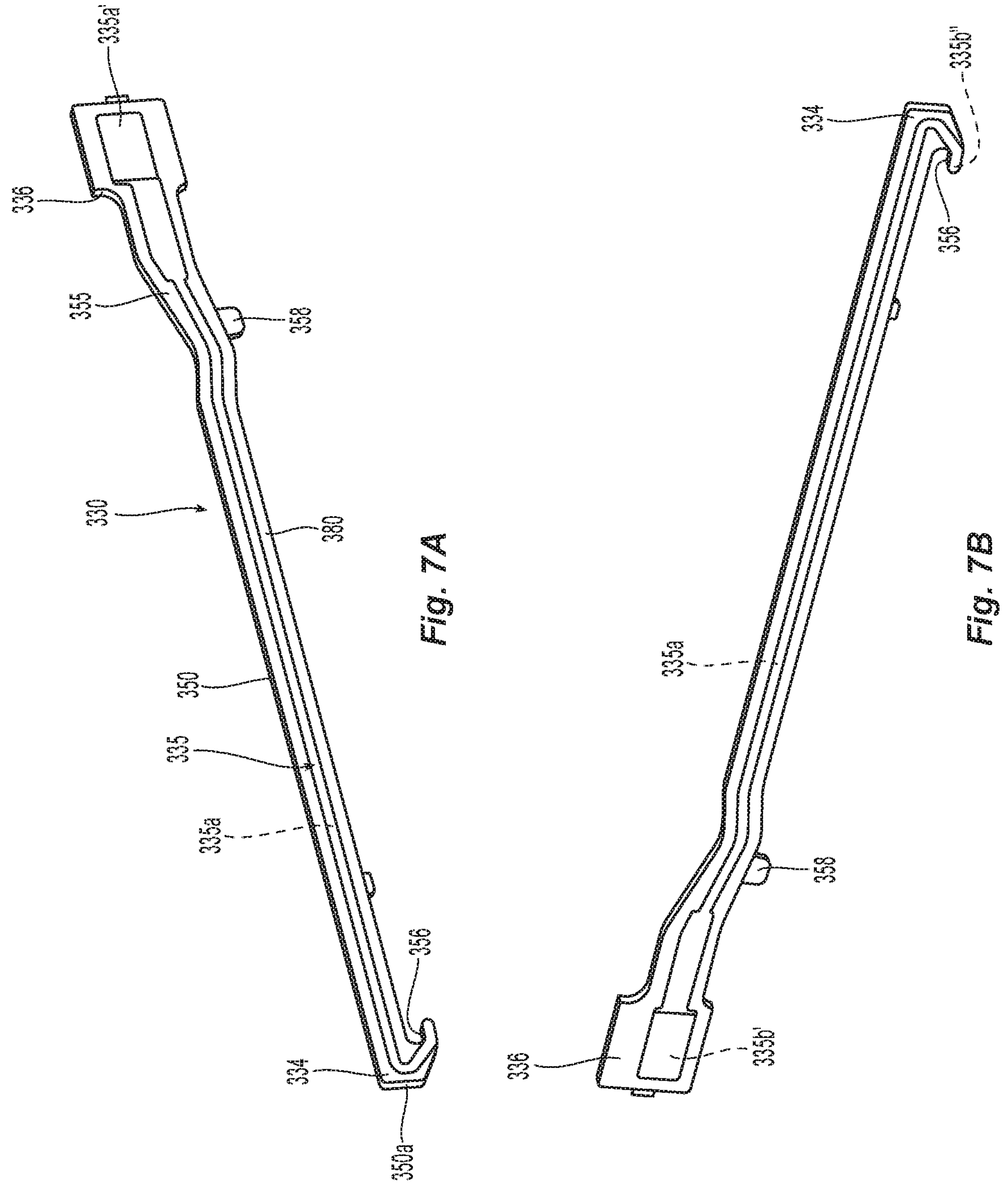
FIGS. 7A-7B are side views of a thermal cutting assembly according to the present disclosure showing resistive elements on either side of a substrate atop an insulator.

FIGS. 7A-7B show one embodiment of a thermal cutting assembly 330 that may be disposed within slot 125 defined in one of the jaw members, e.g., jaw member 120 for cutting tissue disposed between jaw members 110, 120 upon activation thereof. The thermal cutting assembly 330 described herein may be initially manufactured straight and then bent for insertion within slot 125 or may be manufactured in a curved configuration, e.g., similar to the curve of the jaw member 120, and then dropped or placed within slot 125.

FIGS. 7A-7B show an assembled thermal cutting assembly 330 including an elongated substrate 350, a dielectric insulator 355, one or more resistive elements 335 and an encapsulant 380 which, together, form the thermal cutting assembly 330. Substrate 350 may be formed to include one or more mechanical interfaces that facilitate secure engagement within the jaw member 120. For example, a distal end 334 of the substrate 350 may include a hook 356 that depends therefrom and that defines a notch 357 (See FIG. 8A) that is configured to operably engage a portion (not shown) of the jaw member 120. Substrate 350 also includes a rear tab 358 that is configured to operably engage a proximal portion (not shown) of the jaw member 120 upon insertion of the substrate 350 within the slot. Upon insertion of the substrate 350 within the slot 125, the opposing mechanical features operate to retain the substrate 350 securely therein. Further details relating to these mechanically inter-cooperating features are described in concurrently-filed, U.S. Provisional Application Ser. No. [203-14096], entitled "Thermal Cutting Assembly for Mechanical Engagement with a Jaw Member", the entire contents of which being incorporated by reference herein.

As best shown in FIGS. 7A and 7B and as mentioned above, thermal cutter assembly 330 includes a pair of resistive elements 335*a*, 335*b* that extend atop insulator 355 on either side the substrate 350 between a proximal end 336 and the distal end 334 thereof. Disposing resistive elements 335*a*, 335*b* on either side of the substrate 350 rapidly heats the substrate 350 (through the insulator 355) upon activation of the resistive elements 335*a*, 335*b* via activation of conductive pads 335*a*' and 355*b*' that connect to the generator "G" and are activated via switch 90 as explained above. More particularly and as explained above, a proximal end of each resistive element 335*a*, 335*b* is configured to electrically connect to a conductive lead (e.g., similar to leads 133*a*1, 133*b*1 of FIG. 6B) which, in turn, connect to each respective conductive pads 335*a*', 335*b*' and to energy source, e.g., generator "G" (FIG. 1).

Figure 8A:
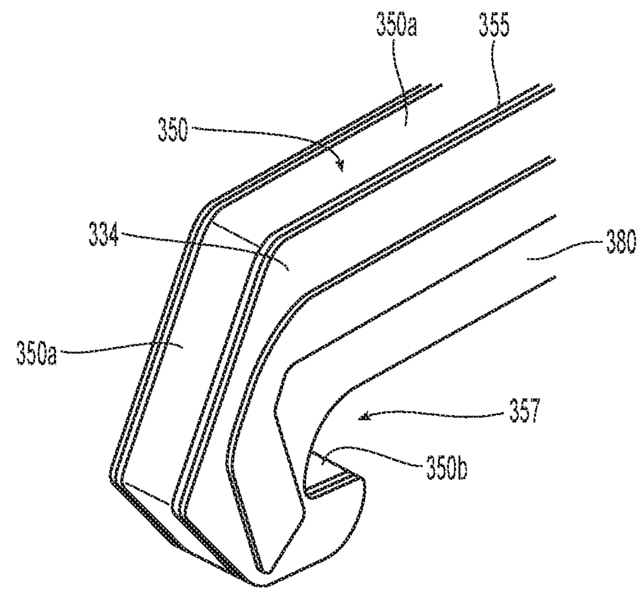
FIG. 8A is an enlarged, front perspective view of the thermal cutting assembly of FIG. 7A showing a conductive bridge disposed between the resistive elements substrate.
Figure 8B:
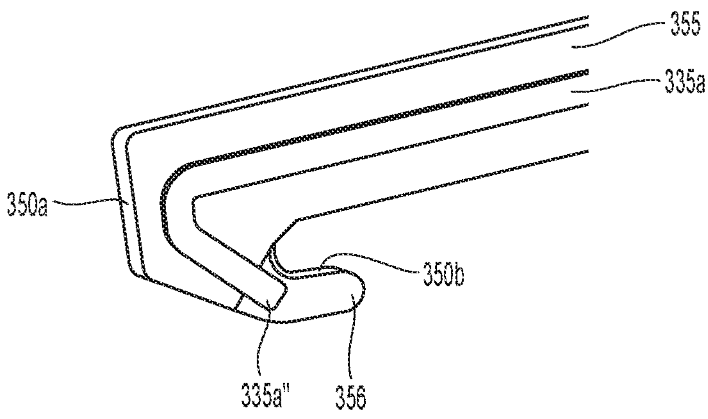
FIG. 8B is an enlarged, side view of the thermal cutting assembly of FIG. 7A showing the conductive bridge disposed on a hook portion thereof.

As shown in FIGS. 8A and 8B, a distal end of the substrate acts as a conductive bridge between the two resistive element 335*a*, 335*b* completing the loop between conductive pads 335*a*', 335*b*'. More particularly, each resistive element 335*a*, 335*b* extends atop and along the dielectric insulator 355 on each side of the substrate 350 towards the distal end 334 thereof towards the hook-like end 356. A distal end, e.g., distal end 335*a*" of resistive element 335*a* and distal end 335*b*" of resistive element 335*b*, is exposed from the dielectric insulator 355 at the hook-like end such that each resistive element 335*a*, 335*b* is disposed in electrical contact with each respective side of the substrate 350 thereby forming and electrical bridge therebetween and completing the electrical circuit back to the generator "G". In other words, the substrate 350 acts as a conductive bridge 350*b* (FIG. 8A) across the width thereof and electrically connects resistive element end 335*a*" with a corresponding resistive element end 335*b*". As mentioned above, resistive elements 335*a*, 335*b* may be composed of a variety of layered conductive and resistive materials to rapidly heat substrate 350 upon activation thereof. As such, the resistive elements 335*a*, 335*b* are electrically connected on either side of the substrate 350 via bridge 350*b* allowing rapid heating thereof upon activation of the resistive elements 335*a*, 335*b*.

An encapsulant 380 may be layered (or otherwise disposed) atop both the dielectric insulator 355 and the resistive elements 335*a*, 335*b* on both sides of the substrate 350. The encapsulant 380 further dissipates heat transfer from the resistive elements 335*a*, 335*b* so that the heat is focused to the cutting edge of substrate 350*a*. The encapsulant 380 may cover bridge 350*b*.

As mentioned above, the substrate 350 includes mechanical retention features, e.g., hook 356 and tab 358, that facilitate engagement and retention within the jaw member, e.g., jaw member 120. During assembly, the hook portion 356 is engaged at an angle to a distal end of jaw member 120 and pulled proximally. The substrate 350 is then properly seated within the slot 125 by angling the substrate 350 in the opposite direction such that the tab 358 engages the proximal portion of the jaw member 120 and secures the substrate 350 within the jaw member 120. When the shaft 12 is thereafter engaged to the jaw member 120 during assembly, the shaft 12 traps the tab 358 in position such that the substrate 350 cannot lift or disengage from the slot 125. Engaging the substrate 350 in this fashion, e.g., simple mechanical fit, helps to minimize thermal conduction from the substrate 350 to the jaw member 120 and the components thereof.

Figure 9A:
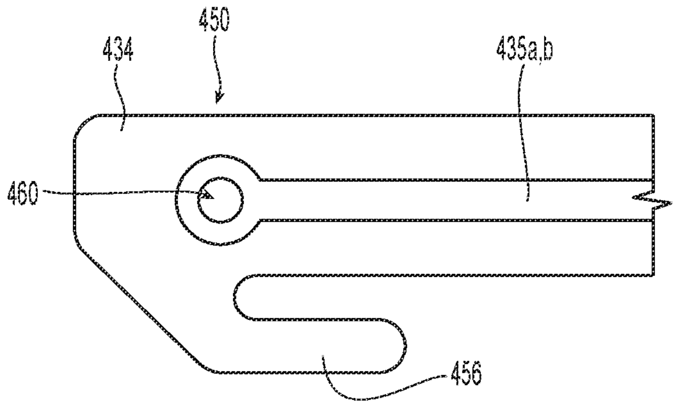
FIGS. 9A-9C are enlarged, side views of another embodiment of a thermal cutting assembly according to the present disclosure showing resistive elements electrically connected via a conductive bridge disposed within a through-hole defined in the substrate.
Figure 9B:
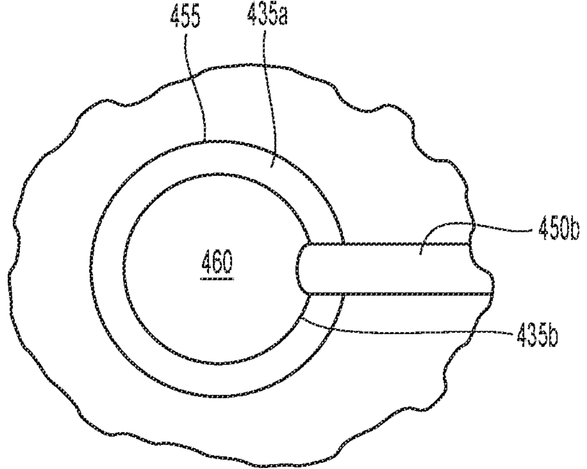
Figure 9C:
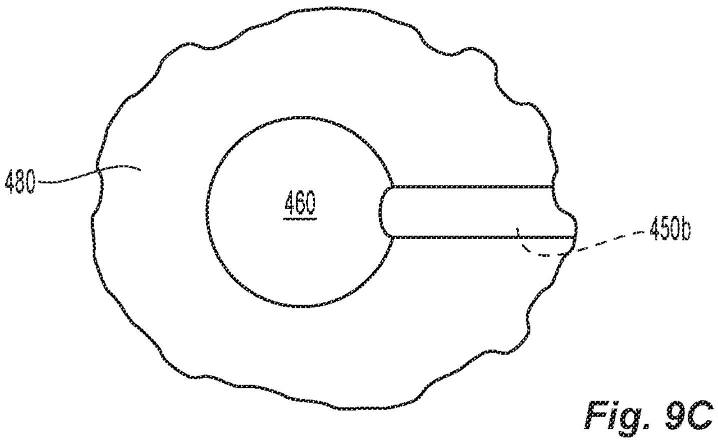

FIGS. 9A-9C show another embodiment of a substrate 450 having a conductive bridge 450*b* disposed through the body thereof. More particularly, substrate 450 may be configured with a through-hole 460 disposed therethrough near a distal end 434 thereof. The conductive bridge 450*b* is disposed within the through-hole 460 and is configured to connect resistive elements 435*a*, 435*b* on either side of substrate 450 (FIG. 9B). Resistive elements 435*a*, 435*b* extend proximally from through-hole 460 to ultimately electrically connect to the generator "G" in a similar manner as described above. The resistive elements 435*a*, 435*b* may be layered atop the dielectric insulator 455 in a similar manner as described above and coated with an encapsulant 480 (FIG. 9C). The dielectric insulator 455 and encapsulant 480 may extend through or partially through the through-hole 460 in such as manner so as to not impede electrical continuity between the resistive elements 435*a*, 435*b* via the conductive bridge 450*b*.

Figure 10A:
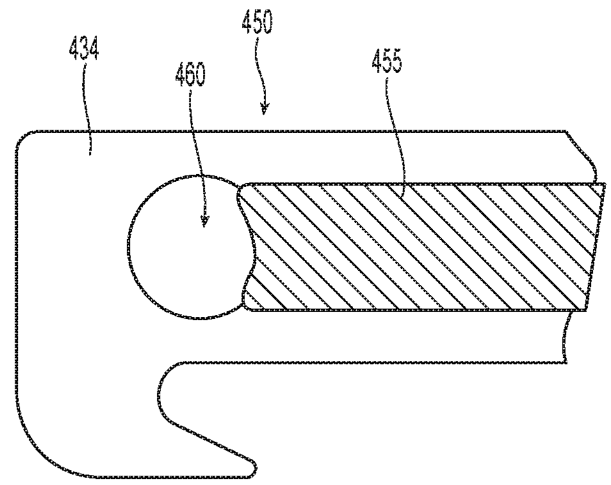
FIGS. 10A-10C are enlarged, side views of another embodiment of a thermal cutting assembly according to the present disclosure showing the various steps for assembling the thermal cutting assembly with the conductive bridge disposed within a through-hole defined in the substrate.
Figure 10B:
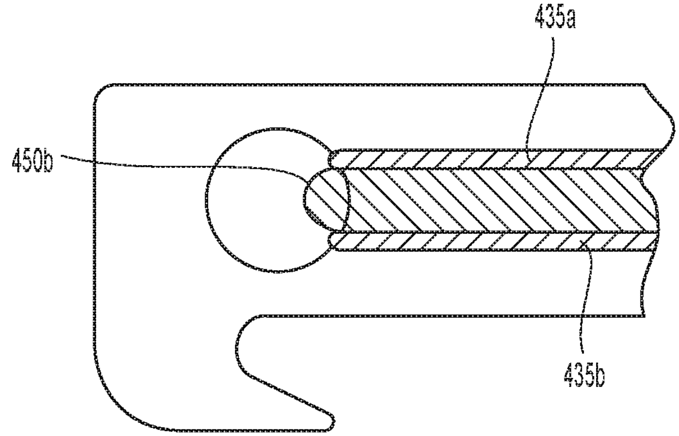
Figure 10C:
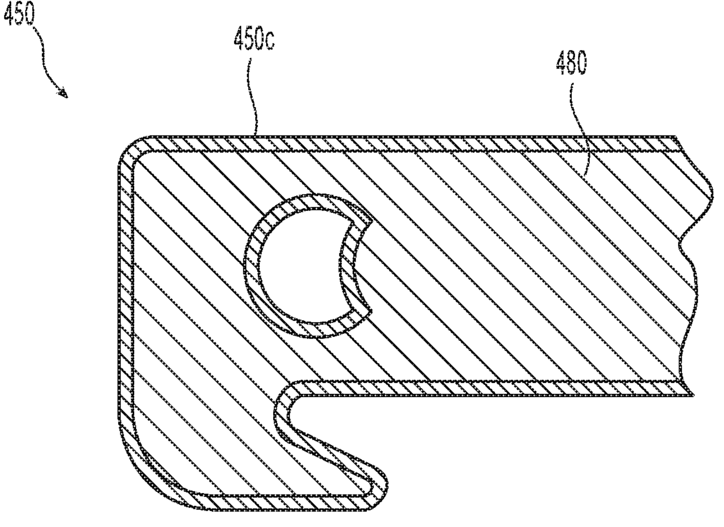

FIGS. 10A-10C illustrate a method of assembling the resistive elements 435*a*, 435*b* atop the dielectric insulator 455 to form the substrate 450 with the conductive bridge 450*b* as described above. More particularly, a dielectric insulator 455 is initially deposited or otherwise attached to the substrate 450 along a side thereof up to the through-hole 460. In a subsequent step, one or more resistive elements, e.g., resistive elements 435*a*, 435*b*, are deposited or otherwise disposed atop the dielectric insulator 455 and are configured to extend to and through the through-hole 460. This allows the resistive elements 435*a*, 435*b* to ultimately connect back to the energy source. Last an encapsulant 480 is added to surround the entire substrate 450 leaving only the exposed cutting edge 450*c* for cutting tissue upon activation thereof.

Figure 11A:
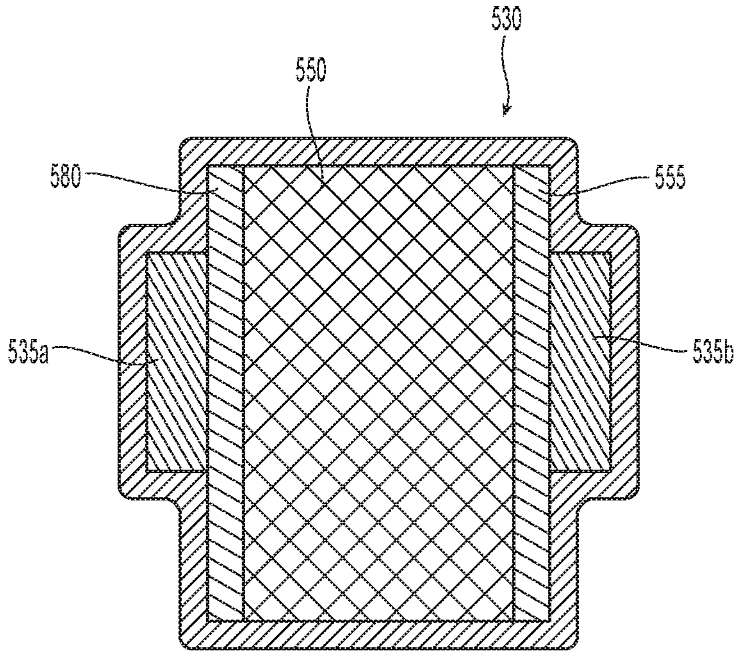
FIGS. 11A and 11B are greatly-enlarged cross sectional views of the thermal cutting assembly showing a dual-sided arrangement for the resistive elements atop the insulator and substrate (FIG. 11A) and a single-sided arrangement (FIG. 11B) for the resistive elements atop the insulator and substrate.

FIG. 11A shows one embodiment of a thermal cutting assembly 530 wherein the resistive elements 535*a*, 535*b* are disposed along opposing sides of the substrate 550. More particularly, each resistive elements, e.g., resistive element 535*a*, is configured to sit atop a dielectric insulator 555 on one side of the substrate 550 and connect to the opposite resistive element, e.g., resistive element 535*b*, disposed on the opposing side of the substrate 550 through a conductive bridge (similar to conducive bridge 450*b* shown above). An encapsulant 580 is added to surround the entire substrate 550 leaving only an exposed cutting edge (not shown) for cutting tissue upon activation thereof.

Figure 11B:
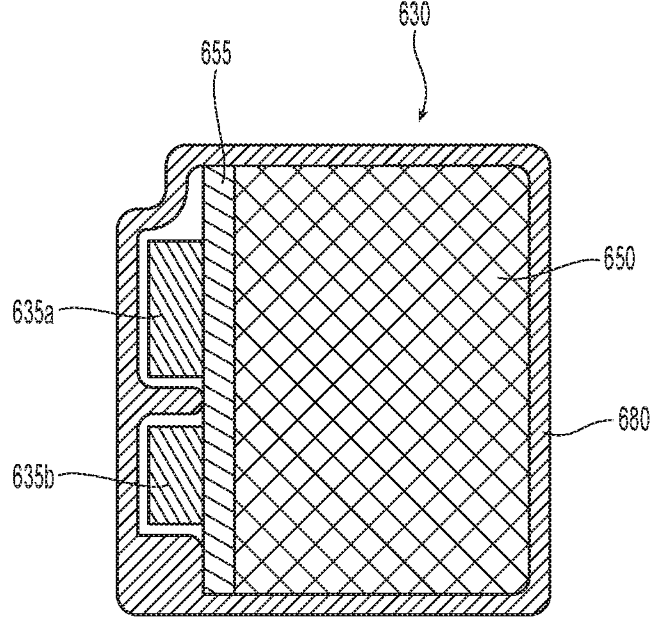

FIG. 11B shows another envisioned embodiment of a thermal cutting assembly 630 wherein the resistive elements

635*a*, 635*b* are disposed along the same side of the substrate 650. More particularly, each resistive element, e.g., resistive element 635*a*, is configured to sit atop a dielectric insulator 655 on one side of the substrate 650 and connect to the opposite resistive element, e.g., resistive element 635*b*, disposed on the same side of the substrate 650. An encapsulant 680 is added to surround the entire substrate 650 leaving only an exposed cutting edge (not shown) for cutting tissue upon activation thereof.

In embodiments, the conductive bridge of any of the above-mentioned resistive elements may be configured to extend around an outside edge of the substrate instead of through a conductive through-hole.

While several embodiments of the disclosure have been shown in the drawings, it is not intended that the disclosure be limited thereto, as it is intended that the disclosure be as broad in scope as the art will allow and that the specification be read likewise. For example, in embodiments, the conductive bridge of any of the above-mentioned resistive elements may be configured to extend around an outside edge of the substrate instead of through a conductive through-hole. Therefore, the above description should not be construed as limiting, but merely as exemplifications of particular embodiments. Those skilled in the art will envision other modifications within the scope and spirit of the claims appended hereto.

What is claimed is:

1. A thermal cutting assembly for a jaw member of a surgical instrument, comprising:

an elongated substrate including proximal and distal ends and a cutting edge disposed along an upper surface thereof;

a dielectric insulator disposed along first and second sides of the substrate and extending at least partially therealong from the proximal end to the distal end thereof;

a first resistive element adapted to connect to an energy source and disposed in thermal communication with the substrate, the first resistive element configured to extend along the dielectric insulator on the first side of the substrate to a distal end portion, the first resistive element including a distal end exposed from the dielectric insulator and in electrical communication with the substrate; and a second resistive element adapted to connect to the energy source and disposed in thermal communication with the substrate, the second resistive element configured to extend along the dielectric insulator on a second side of the substrate to the distal end portion, the second resistive element including a distal end exposed from the dielectric insulator and in electrical communication with the substrate, wherein the substrate forms a conductive bridge between the distal ends of the first and second resistive elements.

2. The thermal cutting assembly for a jaw member of a surgical instrument according to claim 1, further comprising an encapsulant disposed atop the dielectric insulator, the first and second resistive elements and the conductive bridge.

3. The thermal cutting assembly for a jaw member of a surgical instrument according to claim 1, wherein at least one of the first or second resistive elements includes at least one of aluminum, copper, silver, chromium, titanium, stainless steel, nickel, chrome, tin, platinum, palladium, gold, nichrome, and a ferritic iron-chromium-aluminum alloy.

4. The thermal cutting assembly for a jaw member of a surgical instrument according to claim 1, further comprising a hook disposed at the distal end of the substrate, the hook defining a notch configured to operably engage a portion of the jaw member for securing the substrate therein.

5. The thermal cutting assembly for a jaw member of a surgical instrument according to claim 4, wherein the conductive bridge is disposed on the hook.

6. The thermal cutting assembly for a jaw member of a surgical instrument according to claim 4, wherein a distal end of the hook is exposed relative to the dielectric insulator and in electrical communication with the distal ends of both the first and second resistive elements forming the conductive bridge.

7. The thermal cutting assembly for a jaw member of a surgical instrument according to claim 4, wherein the hook defines a notch configured to operably engage a first portion of the jaw member and wherein the conductive bridge defines a portion of the notch.

8. A thermal cutting assembly for a jaw member of a surgical instrument, comprising:

an elongated substrate including proximal and distal ends, a cutting edge disposed along an upper surface thereof, and a through-hole defined through the distal end thereof;

a dielectric insulator disposed along first and second sides of the substrate and extending at least partially therealong from the proximal end to the distal end thereof;

a first resistive element adapted to connect to an energy source and disposed in thermal communication with the substrate, the first resistive element configured to extend along the dielectric insulator on a first side of the substrate to the through-hole, the first resistive element including a distal end disposed in electrical communication with a conductive bridge disposed within the through-hole of the substrate; and a second resistive element adapted to connect to the energy source and disposed in thermal communication with the substrate, the second resistive element configured to extend along the dielectric insulator on a second side of the substrate to the through-hole, the second resistive element including a distal end disposed in electrical communication with the first resistive element via the conductive bridge of the substrate.

9. The thermal cutting assembly for a jaw member of a surgical instrument according to claim 8, further comprising an encapsulant disposed atop the dielectric insulator, the first and second resistive elements and the conductive bridge.

10. The thermal cutting assembly for a jaw member of a surgical instrument according to claim 8, wherein at least one of the first or second resistive elements includes at least one of aluminum, copper, silver, chromium, titanium, stainless steel, nickel, chrome, tin, platinum, palladium, gold, nichrome, and a ferritic iron-chromium-aluminum alloy.

11. The thermal cutting assembly for a jaw member of a surgical instrument according to claim 8, further comprising a hook disposed at the distal end of the substrate, the hook defining a notch configured to operably engage a portion of the jaw member for securing the substrate therein.

12. The thermal cutting assembly for a jaw member of a surgical instrument according to claim 11, wherein the through-hole is distal to the hook.

13. A method of manufacturing a thermal cutting assembly for a jaw member of a surgical instrument, comprising:

disposing a dielectric insulator along first and second sides of a substrate from a proximal end to a distal end thereof, the substrate including a cutting edge disposed along an upper surface thereof and a through-hole defined through the distal end thereof;

depositing a first resistive element on a first side of the substrate atop the dielectric insulator, the first resistive element adapted to connect to an energy source and disposed in thermal communication with the substrate, the first resistive element including a distal end disposed in electrical communication with a conductive bridge disposed within the through-hole of the substrate; and depositing a second resistive element on a second side of the substrate atop the dielectric insulator, the second resistive element adapted to connect to the energy source and disposed in thermal communication with the substrate, the second resistive element including a distal end disposed in electrical communication with the first resistive element via the conductive bridge of the substrate.

14. The method of manufacturing a thermal cutting assembly for a jaw member of a surgical instrument according to claim 13, further comprising depositing an encapsulant atop the dielectric material, the first and second resistive elements and the conductive bridge.

15. The method of manufacturing a thermal cutting assembly for a jaw member of a surgical instrument according to claim 13, wherein at least one of the first or second resistive element includes at least one of aluminum, copper, silver, chromium, titanium, stainless steel, nickel, chrome, tin, platinum, palladium, gold, nichrome, and a ferritic iron-chromium-aluminum alloy.

16. The method of manufacturing a thermal cutting assembly for a jaw member of a surgical instrument according to claim 13, further comprising operably engaging a notch defined within a hook portion of the jaw member to secure the substrate therein.

17. The method of manufacturing a thermal cutting assembly for a jaw member of a surgical instrument according to claim 16, wherein the through-hole is distal to the hook portion.

* * * * *